United States Patent
Mattu et al.

(10) Patent No.: US 6,738,652 B2
(45) Date of Patent: May 18, 2004

(54) CLASSIFICATION AND SCREENING OF TEST SUBJECTS ACCORDING TO OPTICAL THICKNESS OF SKIN

(75) Inventors: Mutua Mattu, Gilbert, AZ (US); Thomas B. Blank, Chandler, AZ (US); Marcy R. Makarewicz, Chandler, AZ (US); Branden Rosenhan, Tempe, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/297,787

(22) PCT Filed: Jun. 6, 2001

(86) PCT No.: PCT/US01/18470

§ 371 (c)(1),
(2), (4) Date: Dec. 9, 2002

(87) PCT Pub. No.: WO01/95800

PCT Pub. Date: Dec. 20, 2001

(65) Prior Publication Data

US 2003/0208111 A1 Nov. 6, 2003

Related U.S. Application Data

(60) Provisional application No. 60/211,852, filed on Jun. 15, 2000, and provisional application No. 60/244,788, filed on Oct. 31, 2000.

(51) Int. Cl.$^7$ ............................................. A61B 5/00
(52) U.S. Cl. ........................ 600/310; 600/473; 600/556
(58) Field of Search ............................ 600/309–310, 600/322, 331, 473–476, 556

(56) References Cited

U.S. PATENT DOCUMENTS

| | | | |
|---|---|---|---|
| 5,377,674 A | 1/1995 | Kuestner | 128/633 |
| 5,725,480 A | * 3/1998 | Oosta et al. | 600/310 |
| 6,456,870 B1 | 9/2002 | Rennert et al. | 600/475 |
| 6,493,566 B1 | 12/2002 | Ruchti et al. | 600/310 |
| 6,512,937 B2 | * 1/2003 | Blank et al. | 600/322 |
| 2001/0021803 A1 | 9/2001 | Blank et al. | 600/322 |
| 2001/0041829 A1 | 11/2001 | Thennadil et al. | 600/322 |

FOREIGN PATENT DOCUMENTS

WO    WO 01/52725    7/2001    ............ A61B/5/00

* cited by examiner

Primary Examiner—Max F. Hindenburg
Assistant Examiner—Matthew Kremer
(74) Attorney, Agent, or Firm—Glenn Patent Group; Michael A. Glenn

(57) ABSTRACT

A method for classifying live subjects according to optical thickness of the skin is based on noninvasive, near-infrared reflectance measurements on skin tissue. An indicator of skin optical thickness is derived through analysis of the water, fat, and protein marker bands in the near infrared spectrum. The skin thickness indicator may then be used to evaluate the suitability of the subject for calibration on a standardized set of optical probes. The optical probes in the standardized set are designed to cover a range of penetration depths by varying the distance distribution between illuminator and detector fibers on each probe tip.

40 Claims, 3 Drawing Sheets

CLASSIFICATION AND SCREENING OF TEST SUBJECTS ACCORDING TO OPTICAL THICKNESS OF SKIN

This application is a 371 of PCT/US01/18470 filed Jun. 6, 2001 and also claims Benefit of Provisional Application Ser. No. 60/211,852 filed Jun. 15, 2000, and Ser. No. 60/244,788 filed Oct. 31, 2000.

FIELD OF THE INVENTION

The present invention relates to characterization of tissue. More particularly the invention relates to methods of classifying a live subject according to optical thickness of skin, utilizing noninvasive NIR spectroscopy techniques.

BACKGROUND OF THE INVENTION

Introduction

For many years near infrared (NIR) spectroscopy has been used in the food and agriculture industries to analyze ground wheat and other turbid samples. See P. Williams, K. H. Norris, eds., *Near Infrared Technology in the Agricultural and Food Industries*, American Association of Food Chemists, St. Paul Minn. (1987). Recently, NIR has found increasing use in biomedical applications, including the nondestructive monitoring of pharmaceuticals and the transcutaneous measurement of analytes in biological tissue. See C. M. Horland, B. Davies, *Proc. SPIE* 1320, 46 (1990). Also see M. R. Robinson, R. P. Eaton, D. M. Haaland, G. W. Koepp, E. V. Thomas, B. R. Stallard, P. L. Robinson, *Clin. Chem.*, 38:1618–1622 (1992); or J. J. Burmeister, M. A. Arnold, G. W. Small, *Diabetes Technology and Therapeutics*, 1:5–16 (2000); or S. F. Malin, T. L. Ruchti, T. B. Blank, S. N. Thennadil, S. L. Monfre, *Clin. Chem.*, 45:1651–1658 (1999) 1999; or O. S. Khalil, *Clin. Chem.*, 45:165–177 (1999). All such applications are possible due to the ability of NIR spectroscopy to extract chemical information from complex, highly scattering materials.

Structure of Human Skin

The structure and pigmentation of human skin vary widely among individuals, as well as between different sites on the same individual. Skin consists of a stratified, cellular epidermis, and an underlying dermis of connective tissue. Below the dermis is the subcutaneous fatty layer or adipose tissue. The epidermis is the thin outer layer that provides a barrier to infection and moisture loss, while the dermis is the thick inner layer that provides mechanical strength and elasticity. The epidermis layer is 10–150 μm thick and can be divided into three layers, the basal, middle and superficial layers. The basal layer borders the dermis and contains pigment-forming melanocyte cells, keratinocyte cells, Langerhan cells and Merkel cells. See Ebling, F. J. *The Normal Skin*. In *Textbook of Dermatology*, 2$^{nd}$ ed.; Rook, A.; Wilkinson, D. S.; Ebling, F. J. G., Eds.; Blackwell Scientific: Oxford, 1972; pp 4–24. The superficial layer is also known as the stratum corneum.

The stratum corneum, the outermost layer of the mammalian epidermis, is formed and continuously replenished by the slow upward migration of aqueous keratinocyte cells from the germinative basal layer of the epidermis. It is replenished about every two weeks in mature adults. See W. Montagna, *The Structure and Function of Skin*, 2$^{nd}$ ed., p 454, Academic, New York (1961). This complex process, involving intracellular dehydration and synthesis of an insoluble protein, keratin, results in keratin-filled, biologically inactive, shrunken cells. These flat, dehydrated, hexagonal cells are tightly bound to their neighbors and each is approximately 30 μm wide and 0.8 μm deep. See Baker, H. *The Skin as a Barrier*. In *Textbook of Dermatology*, 2$^{nd}$ ed.; Rook, A.; Wilkinson, D. S.; Ebling, F. J. G., Eds.; Blackwell Scientific: Oxford, 1972; pp 249–255. There are about 12 to 20 cell layers over most of the body surface. The stratum corneum is typically 10–20 μm thick, except on the palms and soles, where it is considerably thicker. See A. M. Kligman, *The biology of the stratum corneum*, in: *The Epidermis*, W. Montagna, W. C. Lobitz, eds., 387–433 Academic Press, New York (1964).

The major constituent of the dermis, apart from water, is a fibrous protein, collagen, which is embedded in a ground substance composed mainly of protein and glycosaminoglycans. The glycosaminoglycans play a key role in regulating the assembly of collagen fibrils and tissue permeability to water and other molecules. See K. Trier, S. B. Olsen, T. Ammitzboll, *Acta. Ophthalmol.*, 69:304–306 (1999). Collagen is the most abundant protein in the human body. Elastin fibers are also plentiful though they constitute only a small proportion of the bulk. The dermis also contains other cellular constituents, and has a very rich blood supply, though no vessels pass the dermo-epidermal junction. See Ebling, F. J. *The Normal Skin*. In *Textbook of Dermatology*, 2$^{nd}$ ed.; Rook, A.; Wilkinson, D. S.; Ebling, F. J. G., Eds.; Blackwell Scientific: Oxford, 1972; pp 4–24. The blood vessels nourish the skin and control body temperature. In humans, the thickness of the dermis ranges from 0.5 mm over the eyelid to 4 mm on the back and averages approximately 1.2 mm over most of the body. See S. B. Wilson, V. A. Spence, *Phys. Med. Biol.*, 33:894–897 (1988).

Optical Properties of Human Skin

When a beam of light beam impinges on the skin, a part of it is reflected, while the remaining part penetrates the skin. The proportion of reflected light energy is strongly dependent on the angle of incidence. At nearly perpendicular incidence, about four percent of the incident beam is reflected due to the change in refractive index between air ($\eta_D$=1.0) and dry stratum corneum ($\eta_D$=1.55). For normally incident radiation, this specular reflectance component may be as high as seven percent, because the very rigid and irregular surface of the stratum corneum produces off-normal angles of incidence. Regardless of skin color, specular reflectance of a nearly perpendicular beam from normal skin is always between four and seven percent over the entire spectrum from 250–3000 nm. See J. A. Parrish, R. R. Anderson, F. Urbach, D. Pitts, *UV-A: Biologic Effects of Ultraviolet Radiation with Emphasis on Human Responses to Longwave Ultraviolet*, Plenum Press, New York (1978). Only the air-stratum corneum border gives rise to a regular reflection. Results from a previous study indicate that the indices of refraction of most soft tissue (skin, liver, heart, etc) lie within the 1.38–1.41 range with the exception of adipose tissue, which has a refractive index of approximately 1.46. See F. P Bolin, L. E. Preuss, R. C. Taylor, R. J. Ference, *Appl. Opt.*, 28:2297–2303 (1989). Therefore, these differences in refractive indices between the different layers of the skin are too small to produce a noticeable reflection. The differences are expected to be even more insignificant when the stratum corneum is hydrated, because of refractive index matching.

The ninety-three to ninety-six percent of the incident beam that enters the skin is attenuated due to absorption or scattering within any of the layers of the skin. These two processes taken together essentially determine the penetration of light into skin, as well as remittance of scattered light from the skin. Diffuse reflectance or remittance is defined as that fraction of incident optical radiation that is returned from a turbid sample. Absorption by the various skin constituents mentioned above accounts for the spectral extinction of the beam within each layer. Scattering is the only process by which the beam may be returned to contribute to the diffuse reflectance of the skin. Scattering results from differences in a medium's refractive index, corresponding to differences in the physical characteristics of the particles that make up the medium. The spatial distribution and intensity of scattered light depends upon the size and shape of the particles relative to the wavelength, and upon the difference in refractive index between the medium and the constituent particles.

The reduced scattering coefficient of biological tissue depends on many uncontrollable factors, including: concentration of interstitial water, density of structural fibers, and the shapes and sizes of cellular structures. Scattering by collagen fibers is of major importance in determining the penetration of optical radiation within the dermis. See R. R. Anderson, J. A. Parrish, *J. Invest. Dermatol.*, 77:13–19 (1981). The greater the diffusing power of a medium is, the greater the absorption due to multiple internal reflections. Therefore, reflectance values measured on different sites on the same person, or from the same site on different people, can differ substantially even when the target absorber is present in the same concentration. These differences can be attributed to gender, age, genetics, disease, and exogenous factors due to differences in life styles. For example, it is known that, in humans, skin thickness is greater in males than in females, whereas the subcutaneous fat thickness is greater in females. The same group reports that collagen density, the packing of fibrils in the dermis, is higher in the forearms of males than females. See S. Schuster, M. M. Black, E. McVitie, *Br. J. Dermatol.*, 93:63–643 (1975). Due to the wide variation in the amount of collagen present in the dermal layer per unit of volume, physical thickness of the skin is not strictly correlated to the amount of collagen in the dermal layer. Thus, geometric skin thickness alone is not a reliable predictor of the optical properties of an individual subject's skin.

The scattered light remitted from the skin is a mixture of short-path backscattered photons and long-path diffusively scattered photons. The proportion of each is dependent on the separation between the source and detector probes of the spectroscopic instrument. Short-path, backscattered photons dominate the spectral information at small source-detector separations, while long-path, diffusely scattered photons dominate at large source-detector separations. At points closer to the source, the backscattered photons have spent a smaller fraction of their total optical path propagating through the turbid media. At points further from the source, more photons undergo multiple scattering events, and the fraction of their total optical paths spent in the deeper turbid tissue becomes greater. Hence, spectra at large source-detector separations are expected to be heavily weighted by features that correspond to absorbing species located deeper in the tissue. See G. Kumar, J. M Schmitt, *Appl. Opt.* 36:2286–2293 (1997). In summary, for heterogeneous tissue, the spectral characteristics of diffuse remittance are the result of interaction of;

(1) absorption and scattering properties of the tissue;
(2) the distribution of absorbing species and scattering components; and
(3) the source-tissue-detector geometry.

Thus, it would be desirable to adapt probe geometry to maximize the collection of light that has been diffusely reflected from a desired depth or depth range in the skin. Furthermore, it would be a great advantage to classify subjects according to the optical properties of their skin, thus facilitating the screening of those subjects whose skin composition does not match the probe specifications.

SUMMARY OF THE INVENTION

The present invention provides a method for assessment and classification of a subject according to the optical thickness of the skin as determined by noninvasive, near-infrared reflectance measurements on skin tissue. The assignment of this optical skin thickness characteristic is performed by an analysis of the water, fat, and protein marker bands in the near infrared spectrum. The optical skin thickness characteristic is then used to evaluate the suitability of the subject for calibration on a standardized set of optical probes. The optical probes in the standardized set are designed to cover a range of penetration depths by varying the distance distribution between illuminator and detector fibers on each probe tip.

The invention is not limited to the classification of subjects based on the optical thickness of their skin for the noninvasive measurement of blood analytes, but also finds application in diagnosis and investigation of diseases in which a generalized defect of connective tissue is suspected. The measurement of skin thickness, collagen content and density also provides useful information in metabolic and endocrine diseases. See C. Hamlin, R. R. Kohn, J. H. Luschin, *Diabetes,* 24:902–904 (1975) or S. L. Schnider, R. R. Kohn, *J. Clin. Invest.,* 66:1179–1181 (1980).

DETAILED DESCRIPTION

The volar arm measurement site can be characterized as having typical layer thicknesses for the stratum corneum: 0.01 mm (10 $\mu$m), epidermis: 0.1 mm (100 $\mu$m), dermis: 1 mm, and subcutaneous fat: 3–5 mm [22]. See C. Tsai, J. M. Fouke, *Proc. SPIE,* 1888:479–486 (1993). Thus, long wavelength NIR light (1500–1850 nm) can be expected to penetrate through to the subcutaneous fat, while short wavelength NIR (700–1300 nm) light is likely to penetrate to muscle.

Figure 1:
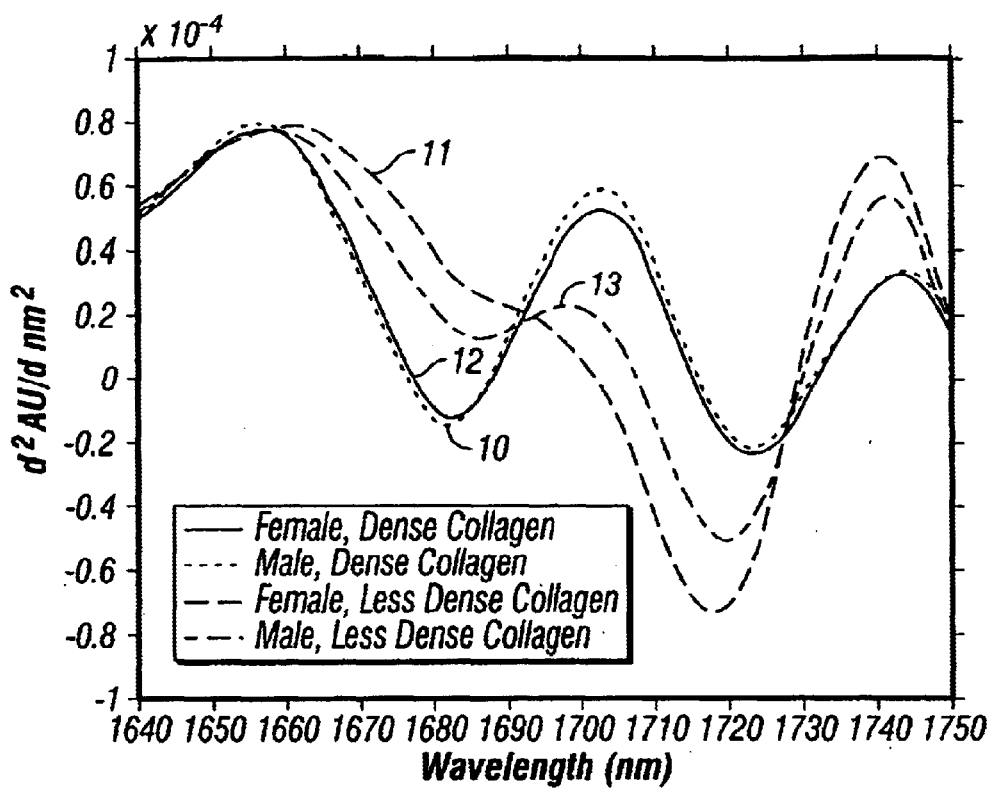
FIG. 1 provides second derivative absorbance spectra of the skin of selected human subjects illustrating variation of collagen density in the skin among the subjects.

The density of collagen, a major constituent of the dermis, can be assessed by comparing the magnitude of the protein band at approximately 1680 nm to the magnitude of the adjacent fat band at approximately 1720 nm. Due to its great diffusing power, dense collagen limits the number of photons penetrating to the subcutaneous fat because the increased scattering coefficient in dense collagen causes an increase in pathlength of light through the dermis. Consequently, the protein absorption increases. Therefore, as FIG. 1 shows, for people having dense collagen, the protein band is more pronounced than for those having less dense collagen. Due to its scattering properties, the collagen within the dermal layer exerts a great influence on the pathlength of protons penetrating the dermis. Thus, collagen density is largely determinant of the optical thickness of the dermis. FIG. 1 shows the second derivative absorbance spectra of people having varying collagen densities. The male subject having dense collagen 10 and the, female subject having dense collagen 12 exhibit the most pronounced protein band, while the female subject with less dense collagen II exhibits the least pronounced protein band. The male subject with less dense collagen 13 exhibits protein bands of intermediate magnitude.

In general, subcutaneous fat is thought to contain low levels of glucose, compared to the dermis and epidermis, which contain glucose from both blood and interstitial fluid. Additionally, characteristic fat spectral features overlap heavily with the glucose bands; multivariate analysis can be used to predict that excessive co-variation of subcutaneous spectral features with those of glucose reduces the net analyte signal available for glucose measurement. See H. Martens, T. Naes, *Multivariate Calibration*; Wiley, New York (1989). Thus, optical sampling of subcutaneous fat is undesirable in noninvasive glucose measurement. Given the severe spectral interference due to the sampling of subcutaneous fat and the low concentration of glucose in subcutaneous fat, it is advantageous to limit the sampling of photons returning from the fat layer. As mentioned above, the probe geometry may be adapted to maximize the collection of light that has been diffusely reflected from a desired depth in the skin. As presented herein, the probe geometry optimizes the penetration depth of the collected light by limiting the range of distances between illumination fibers and the detection fibers. See T. Blank, K. Meissner, F. Grochoki, J. Garside, S. Monfre, Cutaneous targeting optical probe, U.S. patent application Ser. No. 09/887,529 Jun. 8, 2001). However, as discussed above, reflectance values measured on the same site on different people can differ substantially. Thus, in order to sample the desired depth on each and every person the probes would have to be individual specific. The current invention alleviates this problem by providing a method for screening against those individuals whose skin composition does not match the probe specifications.

Screening Algorithm

The invented method employs a screening algorithm that is based on a calculated ratio of the protein to fat band magnitude, using the second-derivative spectrum. Those subjects with a greater protein to fat ratio have a greater likelihood of being calibrated on the instrument. The input to the algorithm is an absorbance spectrum, from which a second derivative is calculated, for the given subject. The second-derivative is calculated using the Savitsly-Golay method. See A. Savitsky, M. J. E Golay, *Anal. Chem,* 36:1627–1639 (1964). The output is an assignment of the subject to a category according to screening status: suitable, moderate, or unsuitable. The output also provides the actual value of the screening ratio (protein to fat ratio) as calculated from the second-derivative spectrum. The categories may be defined as follows:

Suitable—a ratio greater than 0.7.
Moderate—a ratio between 0.6 and 0.7.
Unsuitable—a ratio less than 0.6.

The above category definitions are provided for purposes of description only, and are not intended to be limiting. The skilled practitioner will recognize that the category boundaries can be increased or decreased to alter the sensitivity of the ratio and, consequently, the percentage of clients falling into the different categories.

Calculation of the Protein Band Magnitude

Figure 2:
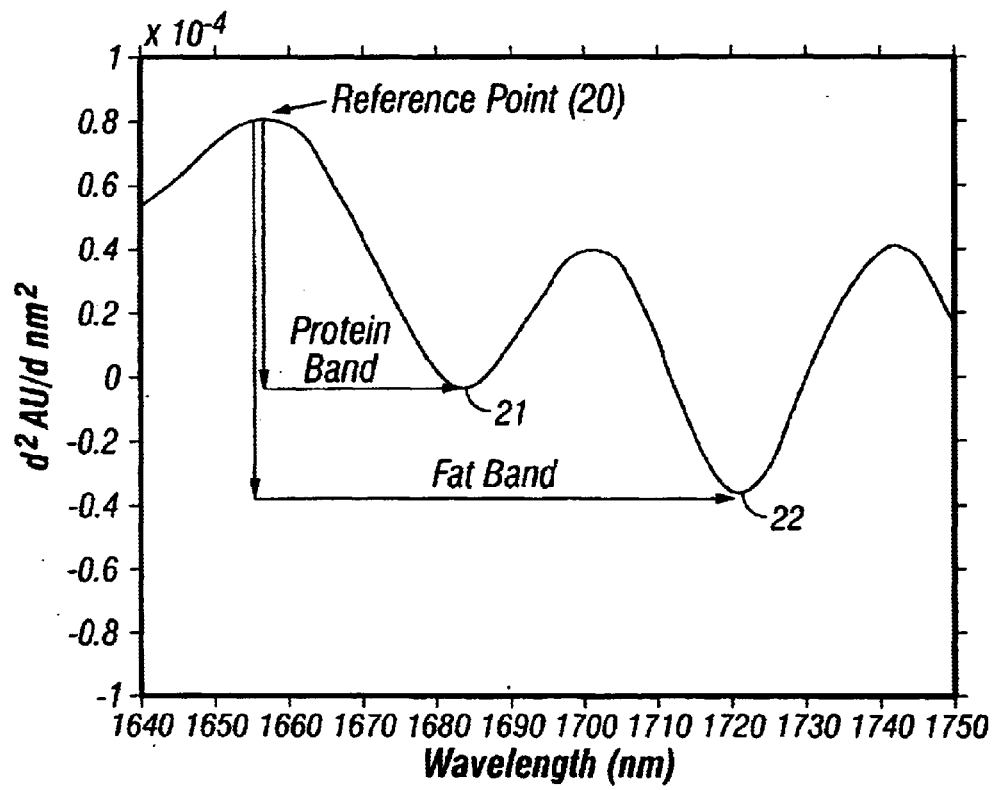
FIG. 2 provides a second derivative absorbance spectrum for determining magnitude of protein band versus fat band, according to the invention.

The protein band magnitude is used to calculate the ratio in the following manner: The second-derivative spectrum contains a near-isobestic region (~1655 nm) for each subject that is used as a reference point to determine the magnitudes of the protein and fat bands. The value of the second derivative at ~1680 nm, the protein band, is subtracted from the value of the reference point at ~1655 nm to determine the protein band magnitude. The reference point 20, the protein band 21 and the fat band 22 are shown in FIG. 2.

The first step in calculating the protein band magnitude is to determine the specific value of the reference point. Then the specific value of the protein feature must be determined. The screening algorithm determines these values and then performs the simple calculation: reference point minus protein point equals protein band magnitude. For spectra without a distinct protein feature, the algorithm returns a value of zero for the protein magnitude because there is no inflection point in the protein feature region.

Calculation of the Fat Band Magnitude

The fat band magnitude is calculated similarly to the protein band magnitude: The value of the second derivative at ~1720 nm, the fat band, is subtracted from the value of the reference point at ~1655 nm to determine the fat band magnitude. All spectra exhibit a distinct fat feature. As with the protein band magnitude, the algorithm performs a simple calculation: reference point minus fat point equals fat band magnitude.

Calculation of the Screening Ratio

Figure 3:
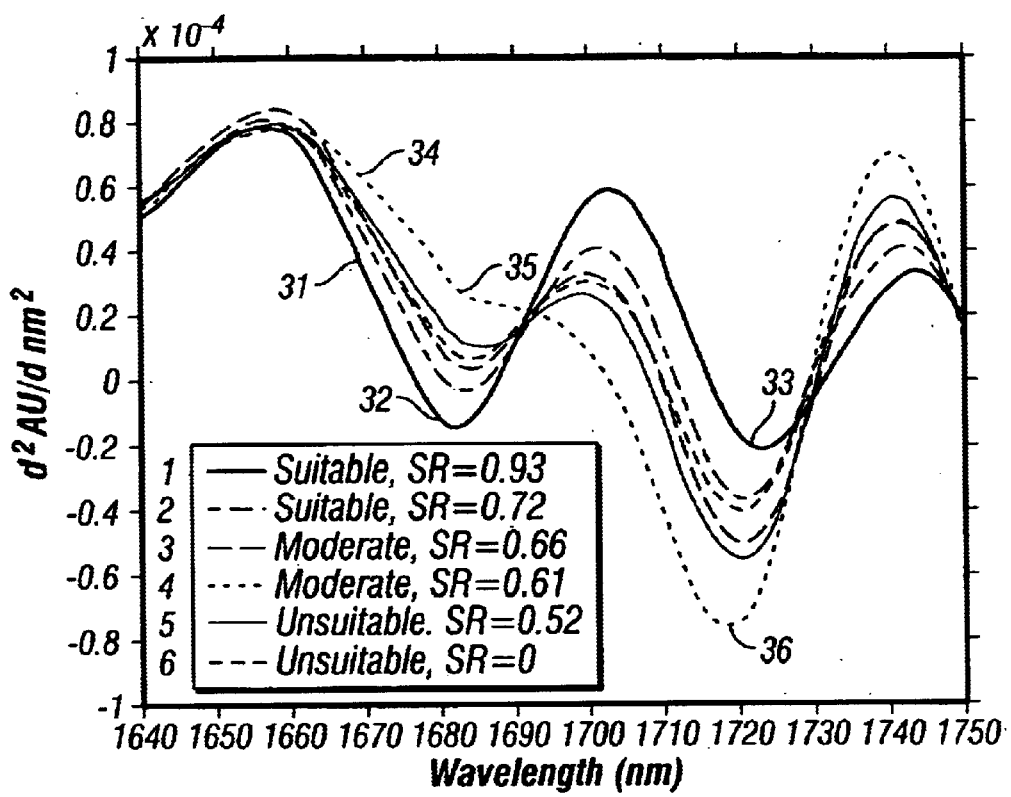
FIG. 3 provides second derivative absorbance spectra for selected human subjects screening ratios and corresponding categories, according to the invention.

The protein to fat ratio is then calculated by simply dividing the protein magnitude by the fat magnitude. FIG. 3 is a plot of second derivative absorbance spectra for different subjects showing some possible screening ratio values corresponding to the 3 screening categories. Subject #1, rated 'suitable,' has a protein-to-fat ratio of 0.93. The corresponding second derivative spectrum 31 displays a pronounced protein band 32, and a fat band 33 of only slightly greater magnitude than the protein band, thus resulting in a protein to fat ratio of slightly less than one: well suited to calibration on the set of optical probes. Subject #6, rated 'unsuitable,' has a protein to fat ratio of 0. In the corresponding second derivative spectrum 34, the protein band 35 is barely evident, while the fat band 36 is very pronounced. Therefore, the resulting protein to fat ratio is substantially zero, because there is no inflection point in the protein band region. Thus the subject is unsuitable as a candidate for calibration.

While it is preferred that the protein band magnitude, the fat band magnitude and the screening ratio be calculated from a second derivative spectrum, one skilled in the art will readily recognize that, in the presence of a protein band of sufficient magnitude to be visualized in the measured spectrum, the protein and fat band magnitudes and the screening ratio may also be calculated from a measured spectrum, without the necessity of calculating the second derivative spectrum.

While the ratio of protein to fat calculated from the magnitudes of the protein and fat bands provides a simple, expedient way of calculating an indicator of the skin's optical thickness, other methods of comparing the magnitudes of the protein and fat bands may be used. For example, chemometric techniques such as multivariate analysis and principle components analysis are suitable. Various other methods of extracting and analyzing spectral data will be apparent to those skilled in the art and are consistent with the spirit and scope of the invention.

Optical Skin Thickness versus Caliper Skinfold Thickness

Figure 4:
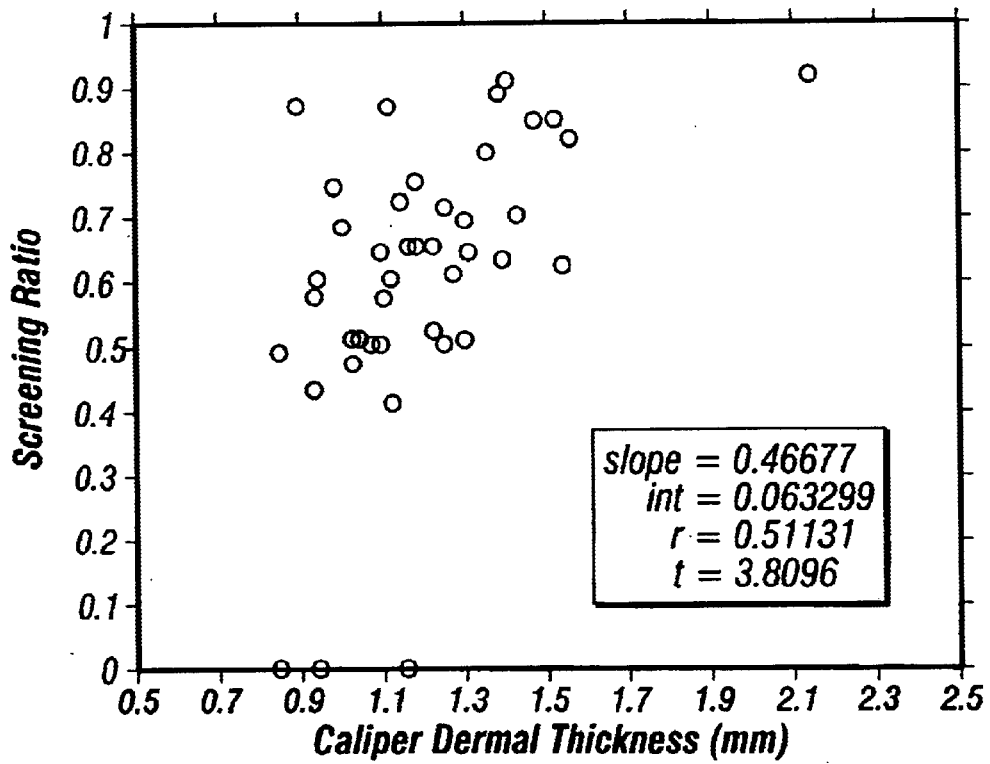
FIG. 4 provides a scatter plot of screening ratio versus caliper skin fold measurement for selected human subjects, according to the invention.

Skinfold calipers have been used to make skinfold thickness measurements, from which body fat estimates have been derived. See J. V. G. A. Dumin, M. M. Rahaman, *Br. J. Nutr.*, 21:681–688 (1967); and J. V. G. A. Dumin, J. Wormersley, *Br. J. Nutr.*, 32:77–97 (1974). However, skinfold measurements do not provide information about the skin's optical thickness. The invention provides a method for assessing the optical thickness of the skin and the density of collagen, a major constituent of the dermis. FIG. 4 provides a scatter plot of screening ratio versus dermal thickness for 43 diabetic subjects. The dermal thickness measurements were made using skinfold calipers of the type known as HARPENDEN, manufactured by British Indicators, LTD. Each skinfold value is the average of five consecutive measurements. As the legend shows, the correlation value between screening ratio and dermal thickness is 0.5113. The low correlation value is evidence that caliper-measured dermal thickness does not necessarily provide information about the optical thickness of the skin.

Figure 5:
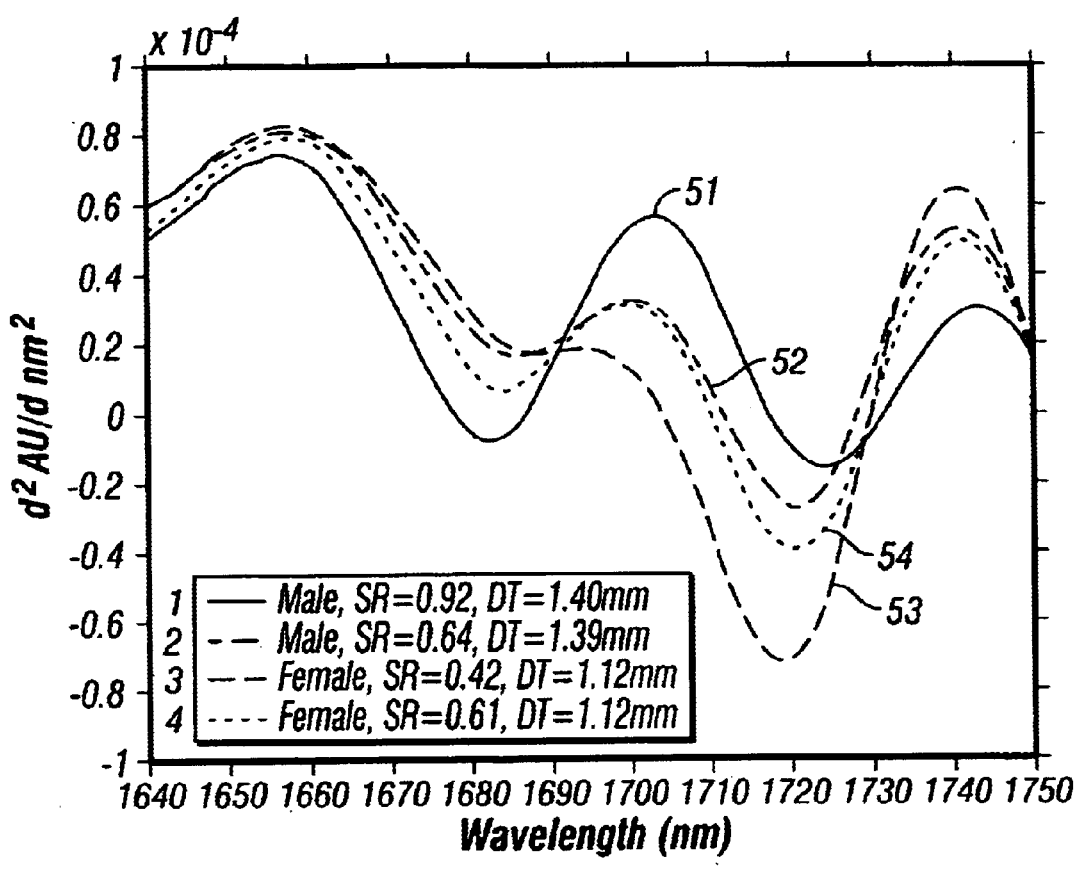
FIG. 5 shows second derivative absorbance spectra along with the screening ratio (SR) and the corresponding caliper-measured dermal thickness (DT) values for selected subjects, according to the invention.

Close inspection of spectra from subjects having similar caliper-measured dermal thickness measurements provides a noteworthy demonstration of the utility of the screening ratio. FIG. 5 shows second derivative spectra for selected subjects having similar caliper-measured dermal thickness (DT) and the corresponding screening ratio (SR) values. For example, subjects 1 and 2, both male, have almost identical DT measurements, 1.40 mm and 1.39 mm, respectively. Yet, their SR values exhibit a pronounced difference: 0.92 and 0.64, respectively. Examination of the respective spectra, 51 and 52, shows a clear difference in the magnitudes of the protein and fat bands. Similarly, subjects 3 and 4, both female, have identical DT values, 1.12 mm and markedly different SR values, 0.42 and 0.61, respectively. The respective spectra, 53 and 54, show similar magnitudes in the protein band, but strikingly different magnitudes in the fat band.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below

What is claimed is:

1. A method of estimating optical thickness of a subject's skin, using noninvasive spectral measurements, comprising the steps of:
   providing a spectrum for a selected site on the skin of said subject;
   comparing magnitude of a protein band in said spectrum with magnitude of a fat band in said spectrum; and
   calculating an indicator of the optical thickness of the skin, based on said compared magnitudes.

2. The method of claim 1, wherein said step of providing a spectrum comprises the steps of:
   noninvasively measuring a NIR absorbance spectrum at said site; and
   calculating a second derivative spectrum from said measured spectrum.

3. The method of claim 1, wherein said step of calculating an indicator of the optical thickness of the skin comprises:
   calculating a ratio of protein to fat at said site from said spectrum.

4. The method of claim 3, wherein said step of calculating a ratio of protein to fat comprises the steps of:
   identifying a reference point in said spectrum;
   determining a value at said reference point;
   calculating the magnitude of the protein band in said spectrum based on the value at the reference point;
   calculating the magnitude of the fat band in said spectrum based on the value at the reference point; and
   dividing the protein magnitude by the fat magnitude.

5. The method of claim 4, wherein said reference point comprises a point within a near-isobestic region in the spectrum.

6. The method of claim 5, wherein said near-isobestic region is at approximately 1655 nm.

7. The method of claim 4, wherein said step of calculating magnitude of a protein band comprises the steps of:
   determining a value at said protein band; and
   subtracting the value at the protein band from the value at the reference point.

8. The method of claim 4, wherein said step of calculating magnitude of a fat band comprises the steps of:
   determining a value at the fat band; and
   subtracting the value at the fat band from the value at the reference point.

9. The method of claim 4, further comprising the step of:
   classifying said subject according to said protein to fat ratio.

10. The method of claim 9, wherein said classifying step comprises:
    assigning said subject into one of a plurality of categories based on said ratio.

11. The method of claim 10, wherein a ratio greater than approximately 0.7 constitutes a first category, a ratio in the range of approximately 0.6 to 0.7 constitutes a second category and a ratio less than approximately 0.6 constitutes a third category.

12. The method of claim 11, further comprising the step of assessing said subjects suitability for calibration on a standardized set of optical probes.

13. The method of claim 12, wherein said optical probes cover a range of penetration depths by varying distance distribution between illuminator and detector fibers on each probe tip.

14. The method of claim 11, wherein said first category includes subjects of high suitability, said second category includes subjects of intermediate suitability and said third category includes those of low suitability.

15. A method of classifying a live subject according to optical thickness of skin, comprising the steps of:
    providing a spectrum for a selected site on the skin of said subject;
    comparing magnitude of a protein band in said spectrum with magnitude of a fat band in said spectrum;
    calculating an indicator of the optical thickness of the skin, based on said compared magnitudes; and
    classifying said subject according to said indicator.

16. The method of claim 15, wherein said step of providing a spectrum comprises the steps of:
    noninvasively measuring a NIR absorbance spectrum at said site; and
    calculating a second derivative spectrum from said measured spectrum.

17. The method of claim 15, wherein said step of calculating an indicator of the optical thickness of the skin comprises:

calculating a ratio of protein to fat at said site from said spectrum.

18. The method of claim 17, wherein said step of calculating ratio of protein to fat comprises the steps of:
identifying a reference point in said spectrum;
determining a value at said reference point;
calculating the magnitude of the protein band in said spectrum based on the value at the reference point;
calculating the magnitude of the fat band in said spectrum based on the value at the reference point; and
dividing the protein magnitude by the fat magnitude.

19. The method of claim 18, wherein said reference point comprises a point within a near-isobestic region in the spectrum.

20. The method of claim 19, wherein said near-isobestic region is at approximately 1655 nm.

21. The method of claim 18, wherein said step of calculating magnitude of a protein band comprises the steps of:
determining a value at said protein band; and
subtracting the value at the protein band from the value at the reference point.

22. The method of claim 18, wherein said step of calculating magnitude of a fat band comprises the steps of:
determining a value at said fat band; and
subtracting the value at the fat band from the value at the reference point.

23. The method of claim 17, wherein said classifying step comprises assigning said subject into one of a plurality of categories based on said ratio.

24. The method of claim 23, wherein a ratio greater than approximately 0.7 constitutes a first category, a ratio in the range of approximately 0.6 to 0.7 constitutes a second category and a ratio less than approximately 0.6 constitutes a third category.

25. The method of claim 24, further comprising the step of assessing said subject's suitability for calibration on a standardized set of optical probes.

26. The method of claim 25, wherein said optical probes cover a range of penetration depths by varying distance distribution between illuminator and detector fibers on each probe tip.

27. The method of claim 25, wherein said first category comprises subjects having high suitability, said second category includes subjects of intermediate suitability and said third category includes those of low suitability.

28. A method of assessing a subject's suitability for calibration or measurement with an optical probe comprising steps of:
providing a spectrum for a selected site on the skin of said subject;
calculating an indicator of the skin's optical thickness from said spectrum; and
classifying said subject according to said indicator.

29. The method of claim 28, wherein said optical probes cover a range of penetration depths by varying distance distribution between illuminator and detector fibers on each probe tip.

30. The method of claim 28, wherein said step of providing a spectrum comprises the steps of:
non-invasively measuring a NIR absorbance spectrum at said site; and
calculating a second derivative spectrum from said measured spectrum.

31. The method of claim 28, wherein said step of calculating an indicator of the skin's optical thickness comprises:
calculating ratio of protein to fat at said site from said spectrum, wherein said ratio is an indicator of the skin's optical thickness.

32. The method of claim 31, wherein said step of calculating ratio of protein to fat comprises the steps of:
identifying a reference point in said spectrum;
determining a value at said reference point;
calculating magnitude of a protein band in said spectrum based on the value at the reference point;
calculating magnitude of a fat band in said spectrum based on the value at the reference point; and
dividing protein magnitude by fat magnitude.

33. The method of claim 32, wherein said reference point comprises a point within a near-isobestic region in the spectrum.

34. The method of claim 33, wherein said near-isobestic region is at approximately 1655 nm.

35. The method of claim 32, wherein said step of calculating magnitude of a protein band comprises the steps of:
determining a value at said protein band; and
subtracting the value at the protein band from the value at the reference point.

36. The method of claim 32, wherein said step of calculating magnitude of a fat band comprises the steps of:
determining a value at said fat band; and
subtracting the value at the fat band from the value at the reference point.

37. The method of claim 31, wherein said classifying step comprises assigning said subject into one of a plurality of categories based on said ratio.

38. The method of claim 37, wherein a ratio greater than approximately 0.7 constitutes a first category, a ratio in the range of approximately 0.6 to 0.7 constitutes a second category and a ratio less than approximately 0.6 constitutes a third category.

39. The method of claim 38, wherein said first category includes subjects of high suitability, said second category includes subjects of intermediate suitability and said third category includes those of low suitability.

40. The method of claim 28, wherein the step of calculating an indicator of the skin's optical thickness from said spectrum comprises:
analyzing spectral data using any of:
chemometric techniques;
multivariate analysis; and
principle components analysis.

* * * * *